United States Patent [19]

Hsieh

[11] Patent Number: 4,968,612
[45] Date of Patent: * Nov. 6, 1990

[54] CONTINUOUS FERMENTATION PROCESS FOR AROMATIC HYDROCARBON BIOCONVERSION

[75] Inventor: Jih-Han Hsieh, Parsippany, N.J.

[73] Assignee: Celgene Corporation, Warren, N.J.

[*] Notice: The portion of the term of this patent subsequent to Oct. 30, 2001 has been disclaimed.

[21] Appl. No.: 635,327

[22] Filed: Jul. 27, 1984

[51] Int. Cl.$^5$ ................................................ C12P 7/44
[52] U.S. Cl. .................................... 435/142; 435/136; 435/143; 435/813; 435/877; 435/253.3; 435/875; 435/876
[58] Field of Search ............... 435/142, 143, 136, 813, 435/877

[56] References Cited

U.S. PATENT DOCUMENTS 4,480,034 10/1984 Hsieh .................................... 435/136

OTHER PUBLICATIONS

Atkinson et al. (1983), pp. 608–613, "Biochemical Engineering & Biotechnology Handbook", The Nature Press.

Kirk–Othmer Encyclopedia of Chemical Technology (1980), 3rd Ed., pp. 874–880.

*Primary Examiner*—Charles F. Warren
*Attorney, Agent, or Firm*—Mathews, Woodbridge & Collins

[57] ABSTRACT

This invention provides a continuous bioconversion process in which a non-growth toluene substrate is bio-oxidized by a specific microbe mutant strain to accumulated extracellular muconic acid at a bioreactor production rate of at least about 5 grams of muconic acid per liter of fermentation medium per hour.

Essential features of the invention process include a continuous feed of whole cell-containing fermentation broth from an auxiliary cell growth and enzyme induction fermentation zone into the main fermentation zone, and a purge stream of whole cell-containing fermentation broth from the main fermentation zone.

8 Claims, No Drawings

CONTINUOUS FERMENTATION PROCESS FOR AROMATIC HYDROCARBON BIOCONVERSION

BACKGROUND OF THE INVENTION

Carboxylic acids are important high volume commodities in the chemical industry. For example, it is estimated that the 1982 worldwide capacity for adipic acid is about five billion pounds.

Adipic acid is produced by oxidation of cyclohexane or cyclohexanol with nitric acid in the presence of a vanadium-copper catalyst. Other methods of synthesizing adipic acid include 1,3-butadiene carbonylation with carbon monoxide followed by hydrolysis; methyl acrylate dimerization; and 1,4-butanediol carbonylation.

Recent biotechnical advances have increased interest in the potential application of bioconversion systems for the production of high volume chemicals such as adipic acid and other commercially established commodities.

One prospective new method of synthesizing a carboxylic acid such as adipic acid is by the hydrogenation of muconic acid, which is a diolefinically unsaturated adipic acid derivative:

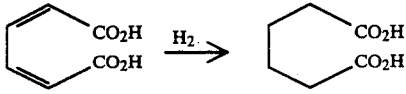

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27, 469–546(1965) by Interscience Publishers.

The Journal of Biological Chemistry, 241(16), 3776 (1966) reports the conversion of catechol and protocatechuate to β-ketoadipate by *Pseudomonas putida*. The conversion of catechol proceeds by the ortho pathway via a muconic acid intermediate:

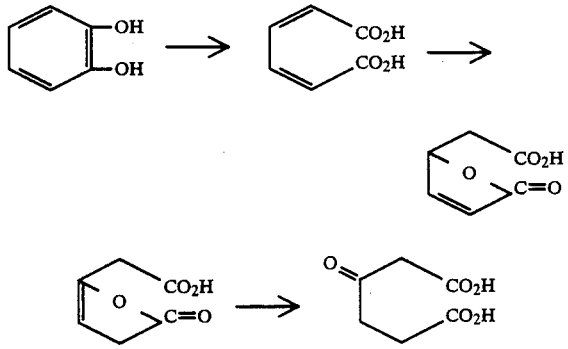

The chemical structures illustrated in the reaction scheme are catechol, muconic acid, muconolactone, β-ketoadipate enollactone and β-ketoadipate, respectively.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through β-ketoadipate to a biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed β-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an aromatic hydrocarbon substrate such as toluene by the ortho pathway via muconic acid and β-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation.

The said construction of the desirable mutant strains recently has been achieved, as exemplified by *Pseudomonas putida* Biotype A strain ATCC No. 31916 and genotypically related mutants.

As a consequence of the prospect of large scale bioconversion systems for production of carboxylic acid type compounds from lower cost hydrocarbon substrates, the problems of fermentation system stability, effective biocatalyst activity and consequential bioconversion product formation and accumulation, and of efficient recovery of extracellular bioconversion products contained in fermentation culture media are of increasing significance. The product inhibition of enzymatic activity by an accumulated carboxylic acid metabolite in a fermentation medium is a serious obstacle to high rate production of the carboxylic acid metabolite as a desired product of the process.

Accordingly, it is an object of this invention to provide a bioconversion process for converting a nongrowth aromatic hydrocarbon to an extracellular accumulated quantity of carboxylic acid metabolite with a sustained high level of biocatalytic activity.

It is a further object of this invention to provide a continuous fermentation process for bio-oxidation of toluene via the ortho pathway to accumulated extracellular muconic acid with a sustained high reactor productivity, and to provide for the recovery of the accumulated muconic acid product.

Other objects and advantages of the present invention shall become apparent from the accompanying description and examples.

DESCRIPTION OF THE INVENTION

One or more objects of the present invention are accomplished by the provision of a continuous bioconversion process which comprises (1) continuously feeding toluene, an aqueous nutrient stream and molecular oxygen into a first fermentation zone containing a microorganism which bio-oxidizes the toluene to accumulated extracellular muconic acid product at a production rate of at least about 5 grams of muconic acid per liter of fermentation medium per hour; (2) continuously withdrawing whole cell-containing fermentation broth from the first fermentation zone and passing the withdrawn fermentation broth through a cross-flow membrane filtration zone to provide a whole cell-containing retentate stream and a cell-free muconic acid-containing permeate stream from the filtration zone; (3) recycling the retentate stream to the first fermentation zone, and recovering muconic acid product from the cell-free permeate stream; (4) continuously feeding toluene, an aqueous nutrient stream and molecular oxygen into a second fermentation zone containing the same microorganism as in the said first fermentation zone, under toluene-limited and growth carbon-limited conditions which favor cell growth and enzyme induction in the second fermentation zone; (5) continuously withdrawing a stream of whole cell-containing fermentation broth from the second fermentation zone and continuously passing the said stream into the first fermentation zone; and (6) withdrawing a purge stream of first fermentation zone whole cell-containing broth out of the fermentation system, at a monitored withdrawal rate for control of cell concentration and the muconic acid productivity level in the said first fermentation zone.

The non-growth toluene feed stream can be partially or completely replaced by benzyl alcohol, benzaldehyde, benzoic acid, catechol, or mixtures thereof. Each compound is capable of quantitative bioconversion to accumulated extracellular muconic acid.

The term "non-growth" as employed herein refers to toluene or equivalent carbon source which is bio-oxidized to muconic acid, but not to biomass for cell growth.

The term "nutrient stream" or "nutrient medium" as employed herein refers to an aqueous solution of inorganic and organic compounds which provide carbon, nitrogen, sulfur, phosphorus, iron, magnesium, and other elements essential for cell growth and viability. Typical nutrient formulations are illustrated in Tables 1-2 of the Examples.

The term "product inhibition" as employed herein refers to the inhibition of enzymatic activity and the suppression of enzyme induction caused by the presence of an accumulated quantity of a specific metabolite product, such as muconic acid.

The term "toluene-limited" as employed herein refers to a toluene content in the second fermentation zone which is limited to not more than about 0.1 millimole of toluene dissolved in the fermentation medium, such as between about 0.01–0.1 millimole of toluene.

The term "growth-carbon limited" refers to a growth carbon content in the second fermentation zone which is limited to not more than 0.5 millimole of acetate or equivalent growth carbon source dissolved in the fermentation medium, such as between about 0.01–0.5 millimole of acetate or equivalent carbon source.

The term "nutrient-limited" as employed herein refers to an essential fermentation parameter with respect to cell stability, as illustrated in the Examples. Nutrient-limitation is more fully described in copending patent application Serial Number 483,796, filed Apr. 11, 1983 (incorporated by reference).

For a *Pseudomonas putida* Biotype A strain ATCC No. 31916 type of mutant strain, the cells grow on a preferred growth carbon and energy source (glucose, succinate or acetate) and convert a non-growth carbon substrate (e.g., toluene) to a metabolite product (e.g., muconic acid). The mutant strain prefers not to grow on toluene as a carbon source. However, in the presence of toluene and other nutrients over a prolonged period of time (3–4 days), the mutant strain population has the tendency to "revert"; i.e., exhibit the ability to grow on toluene again. Initially a small population of the cells reverts, and eventually the majority of the cell population reverts. This reversion problem is a characteristic of many of these genetically manipulated microorganism populations in bioconversion systems.

The application of nutrient-limitation to suppress this reversion phenomenon in bioconversion systems is novel. Thus, for microbial bioconversion processes, the nutrient-limitation aspect can be applied not only to achieve steady state production of cells and product, but also to improve the stability of cells.

Further, it has been found that high reactor productivity for muconic acid production requires the removal of the excess energy generated by the bioconversion. During a continuous fermentation with cell recycle, a minimal amount of growth carbon and other nutrients is necessary for maintenance, and for growth as an energy sink to remove the excess energy generated.

Microorganism

As noted in the Background Of The Invention section above, the microbiological oxidation of toluene to accumulated muconic acid requires the construction of mutant strains of microorganisms, e.g., as exemplified by *Pseudomonas putida* Biotype A strain ATCC 31916 and related variants.

This type of mutant strain can be provided by a process for microorganism construction which comprises (1) culturing microorganism species selectively to provide strain A1 which metabolizes toluene by the ortho pathway via catechol to muconic acid, and which subsequently metabolizes the resultant muconic acid via β-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

The starting microorganism can be any microbe capable of growth on toluene or catechol and which possesses a catechol 1,2-oxygenase, e.g., a Pseudomonad. A variety of naturally occurring organisms have these traits including some members of the species *Pseudomonas putida, Pseudomonas aeruginosa, Pseudomonas fluorescens;* some members of the genera *Azotobacter* and *Nocardia;* and a number of unclassified fungi (both molds and yeasts).

The preferred constructed microorganisms are those described in U.S. Pat. No. 4,355,107, which possess a novel combination of enzymes which include (1) dihydrodihydroxybenzoate dehydrogenase; and (2) catechol 1,2-oxygenase with activity that is not inhibited in the presence of a low level (e.g., less than about five grams/liter) of muconic acid in a growth medium.

Illustrative of suitable microorganisms are constructed strains of fluorescent Pseudomonads each of which has the following characteristics:
(a) possesses catechol 1,2-oxygenase enzyme with activity that is not inhibited in the presence of a low level of muconic acid in a growth medium;
(b) lacks active catechol 2,3-oxygenase;
(c) lacks active muconate lactonizing enzyme; and
(d) cells are rod shaped, vigorously motile and polarly flagellated.

First Fermentation Zone

The fermentation conditions in the first fermentation zone are selected and maintained for sustained maximum biocatalyst activity and muconic acid productivity.

Growth nutrient-limitation is necessary in order to achieve a "steady state", i.e., a constant level of cell concentration and muconic acid productivity in the continuous flow reactor with a defined medium composition. The limited nutrient can be growth carbon, nitrogen, phosphate, sulfate, potassium, magnesium or any other growth-requiring trace metals, or oxygen in the case of the present invention aerobic fermentation.

An important advantage of the present invention process is the reduction of toluene repression on enzyme synthesis in the first fermentation zone, as a consequence of the choice of microorganism and the controlled balance of bioconversion conditions. Another advantage is the suppression of product inhibition of enzymatic activity in the second fermentation zone, as a consequence of the low concentration of product in the second fermentation zone.

In a typical operation, the cell concentration in the first fermentation zone is maintained at a level between about 6-12 grams per liter of fermentation medium.

The biocatalytic activity level (i.e., the specific productivity) in the first fermentation zone is at least about 0.5 gram of muconic acid production per dry weight gram of cells per hour.

The toluene is converted to muconic acid with a reactor productivity of at least about 5 grams of muconic acid per liter of fermentation medium per hour.

The concentration of muconic acid in the first fermentation zone is controlled within the range between about 20-30 grams per liter of fermentation medium.

The toluene content in the first fermentation zone is in the range between about 0.3-1.5 millimoles of toluene dissolved in the fermentation medium.

The growth carbon content in the first fermentation zone is limited to not more than about 0.5 millimoles of acetate or equivalent growth carbon source dissolved in the fermentation medium, i.e., between about 0.01-0.5 millimole of acetate or equivalent carbon source.

The bioconversion in the first fermentation zone normally is conducted at ambient temperatures up to about 31° C. Approximately neutral pH conditions are maintained in the first fermentation zone by the addition of a basic reagent, preferably ammonium hydroxide. The muconic acid product is present in the fermentation broth in the form of a water-soluble muconate salt, such as ammonium muconate.

As noted previously, whole cell-containing fermentation broth is withdrawn continuously from the first fermentation zone and passed through a cross-flow membrane filtration zone.

The cross-flow membrane filtration system employed can be selected from the various hollow fiber, tube, plate and frame, and spiral wound types of modular ultrafiltration systems which have been developed and are available as commercial products.

Romicon (Woburn, Mass.) markets polysulfone membrane hollow fiber or tube ultrafiltration systems. Millipore (Bedford, Mass.) has available plate and frame cassette and spiral wound modular ultrafiltration systems, with cellulosic polymer, polysulfone and polyimide types of membranes. Dorr-Oliver (Westport, Conn.) sells a plate and frame ultrafiltration system with a polysulfone type of membrane. Other commercially available cross-flow filtration systems are produced by companies such as Osmonics (Minnetonka, Minn.), DDS (Nakskov, Denmark), Abcor (Wilmington, Mass.), Nuclearpore (Calif.) and N-D-A (New York).

The resultant whole cell-containing retentate stream from the filtration zone is recycled to the first fermentation zone.

The resultant cell-free muconate-containing permeate stream from the filtration zone is subjected to further processing for recovery of the muconic acid content.

The muconic acid product can be recovered from the cell-free permeate stream by any technique suitable for isolating an organic carboxylic acid solute from an aqueous medium. Illustrative of a procedure for product recovery, a permeate stream containing soluble muconate salt (e.g., ammonium muconate) is acidified with a reagent such as sulfuric acid or phosphoric acid to convert the muconate salt to its free acid form. Under the acidic conditions (e.g., a pH of less than about 3) the muconic acid product precipitates out of solution (solubility less than 0.02 weight percent). It is readily separated from the aqueous fermentation medium by filtration or other conventional means.

The first fermentation zone bioconversion can be operated as a continuous muconic acid production system for an extended period (e.g., 20-40 days), with the proviso that the selected microorganism mutant strain population does not revert during the fermentation, so as to grow on the toluene carbon source and diminish the productivity of muconic acid, and that there is no loss of biocatalytic activity.

Second Fermentation Zone

The function of the second fermentation zone is to provide a constant source of actively induced whole cell-containing fermentation broth for continuous transfer into the first fermentation zone.

The fermentation conditions in the second fermentation zone are optimized for fast cell growth and enzyme induction in the cells.

The toluene in the second fermentation zone is limited to not more than about 0.1 millimole (i.e., between about 0.01-0.1 millimole) of toluene dissolved in the fermentation medium.

The growth carbon in the second fermentation zone is limited to not more than about 0.5 millimole (i.e., between about 0.01-0.5 millimole) of acetate or equivalent growth carbon source dissolved in the fermentation medium.

In a typical operation, the steady state cell concentration is about 3-5 grams per liter with the provision of required nutrient salts, and the muconic acid concentration is about 10-15 grams per liter of fermentation medium.

The actively induced cells at a specific growth rate of about 0.01–0.4 reciprocal hour (equal to the dilution rate) is fed as a continuous stream from the second fermentation zone to the first fermentation zone. Fresh membrane-sterilized deionized water is pumped into the second fermentation zone at a rate sufficient to maintain a constant volume of fermentation broth in the second fermentation zone.

Purge Stream

An essential aspect of the invention process is the provision of a purging function relative to the first fermentation zone medium which contains whole cells and accumulating metabolic byproducts.

The volume of purge stream withdrawal of whole cell-containing first fermentation zone broth is monitored to establish control of the steady state cell concentration level and the steady state muconic acid productivity level in the first fermentation zone.

In a typical operation, the cell-containing purge stream is withdrawn from the first fermentation zone in a volume per hour which corresponds to about 1–10 percent of the continuous feed stream volume into the first fermentation zone.

The present invention continuous process with a two-zone fermentation system is an improvement over the continuous type of one zone fermentation process illustrated in Example V.

In the practice of the present invention process, reactor productivity (STY) is optimized by the continuous supply of actively induced cells to the first fermentation zone, whereby high levels of biocatalyst activity and reactor productivity are maintained in the first fermentation zone.

This balance of advantages is not characteristic of conventional batch or continuous modes of bioconversion systems. In each of these types of fermentation systems, the whole cells are in constant contact with a high concentration of toluene and accumulated metabolite product, in order to achieve high reactor productivity with a concomitant risk of product inhibition of enzymatic activity and suppression of enzyme induction.

The following examples are further illustrative of the present invention. The components and specific ingredients are presented as being typical, and various modifications can be derived in view of the foregoing disclosure within the scope of the invention.

For cultivation, carbon sources such as glucose, succinate or acetate, and nutrients are added aseptically prior to inoculation. Incubation conditions are in 250 ml shake flasks. Shaking is in a rotary shaker with temperature controlled at 28° C.

Growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophotometer or with High Performance Liquid Chromatography (HPLC).

Cultures are stored under liquid nitrogen.

EXAMPLE I

This Example illustrates the construction of a strain of microorganism which oxidizes toluene via the ortho (β-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene-containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31916 type of mutant strain in accordance with the procedure described in U.S. Pat No. 4,355,107.

Strain MW 1210 of Example I is subjected to continuous cultivation with toluene as the sole source of carbon. Initially a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile deionized water. An aliquot of these cells is transferred to fresh medium containing 0.5 mM p-hydroxybenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

One isolate, designated MW 1211.1, is employed in the Examples III–IV process embodiments of the present invention.

EXAMPLE III

This Example illustrates a continuous fermentation process embodiment for the production of muconic acid from toluene in accordance with the present invention.

A. First Fermentation Zone

1. Inoculum Preparation

A *Pseudomonas putida* Biotype A strain ATCC No. 31916 culture (regular "NO" medium aqueous culture in polypropylene vial stored frozen in liquid nitrogen) is thawed and transferred (0.5–1.0 ml) to a 250 ml shake flask containing 50 ml of regular "NO" medium (Table 1) with 20 mM sodium acetate as the growth carbon source, and is incubated at 30° C. (250 RFM) for 16 hours to an optical density of 90–100 klett units. Six shake flasks (with a total of 300 ml inoculum) are inoculated aseptically into a 16 liter steam sterilizable fermentor (New Brunswick Scientific, Model SF 116) containing 11.5 liters of sterilized LP-2 (Table 1) medium with 20 mM of sodium acetate to start fermentation.

2. Cell Growth/Enzyme Induction

After the inoculation, the cells are allowed to grow for 8–10 hours to an optical density of 40–60 klett units. Toluene is then supplied to the first fermentation zone medium in vapor phase via air (0.2 micron filter sterilized and inlet pressure 20 psig) stripping at an air-toluene vapor rate of 125 cc/min. The toluene saturated air stream contains 3.7 mole percent toluene based on toluene vapor pressure at ambient 25° C.

The fermentation temperature is controlled at 30° C., the pH at 6.9 with 5 M ammonium hydroxide and 3 M sulfuric acid solutions, and the dissolved oxygen at 30–90 percent saturation with 600 RPM agitation and 5 liter/min aeration (or approximately 0.5 VVM, volume of air/volume of fermentation broth/minute, inlet air pressure 20 psig). Pluronic L61 polyol (BASF) is used as an antifoam agent.

As the optical density of the fermentation medium reaches 60–90 klett units (about 10–12 hours after inoculation), an aqueous solution of heat-sterilized Feed I (Table 2) containing 200 g/l acetic acid, 2.27 g/l $Na_2HPO_4$, 4.36 g/l $KH_2PO_4$, 31 g/l KOH and 22.2 g/l NaOH is added (FMI Piston Positive Displacement pump) to the first fermentation zone at a rate of 0.2 ml/min (a fed-batch mode of fermentation). The air-toluene vapor rate is increased to 250 cc/min and the Feed I rate to 0.4 ml/min as the optical density reaches 300 klett units. The air-toluene vapor rate and the Feed I are further increased to 0.6 ml/min and 500 cc/min, respectively, as the optical density reaches 600 klett units. The air-toluene rate is increased to 750 cc/min and then to 1000 cc/min as the optical density reaches 750 klett units, and an aqueous solution of heat-sterilized Feed II (Table 2) containing 53.9 g/l $(NH_4)_2SO_4$, 17.7 g/l $MgSO_4.7H_2O$, 0.7 g/l $CaCl_2.2H_2O$ and 0.4 g/l $FeSO_4.7H_2O$ is added to the first fermentation zone medium at a rate of 0.6 ml/min.

During this cell growth/enzyme induction fed-batch fermentation stage, toluene concentration in the fermentor exit gas ranges is between 0.01–0.05 mole percent. About 28 to 30 hours after the inoculation, the broth optical density reaches 900–1000 klett units (or 3.2–3.5 g/l cell concentration) and the fermentation is converted from the fed-batch mode fermentation to a continuous mode with cell (biocatalyst) recycle input from the filtration zone.

3. Continuous Fermentation With Cell Recycle

Commencing the continuous/cell recycle fermentation mode, fresh membrane-sterilized deionized water is pumped (Micro centrifugal gear pump) into the first fermentation zone at a rate of 15–18 ml/min. The fermentation broth is pumped from the fermentor with an internal circulation pump (Flojet low shear diaphragm pump) to a sterilized Romicon hollow tube ultrafilter with a polysulfone type ultrafiltration membrane (PM-100; molecular weight cut-off of 100,000). Total membrane area is 1.1 $ft^2$ (50 tubes with inside diameter 0.043 inch in a 1.0 inch×25 inches cylindrical polypropylene cartridge with epoxy type seal at both ends of the cartridge,.

The fermentation broth cells is "cross-flow" filtered at a permeate(cell-free product stream) rate of 18–20 ml/min. The fermentation broth with cells is continuously circulated through the ultrafilter at an internal circulation rate of 0.5–1 l/min and a pressure drop of 3–5 psig across the ultrafiltration membrane. The membrane module is vertically situated and the fermentation broth is pumped upward to ensure maximal flux and minimal membrane fouling.

During the transition from fed-batch to continuous with cell recycle, both the Feed I and Feed II addition rates are increased to 0.9 ml/min. An automatic on-line measurement and process computer control system is activated to control the fermentor exit gas toluene concentration at 0.5 mole percent (corresponds to an equilibrium liquid phase dissolved toluene concentration of 0.55 mM toluene) with a Texas Instrument PM-500 programmable controller. The controller activates a ProMinent electronic pump in response to controller set point to pump additional liquid toluene to the fermentor. An initial toluene pump rate range equivalent to 0.29–0.57 ml/min liquid toluene is programmed. The pumped additional liquid toluene is combined with the 1000 cc/min air-toluene stream before feeding into the fermentor broth. A pure oxygen stream (membrane filter-sterilized at 40 psig) is metered into the fermentor at 100 cc/min with the main air sparger.

The liquid volume in the first fermentation zone is controlled at a level of about 11.5 liters.

4. Continuous Fermentation With Second Fermentation Zone Input

Sixteen hours after starting the continuous mode with cell recycle operation without purge, the cell concentration in the first fermentation zone is 8.1 g/l and the muconic acid product concentration is 15.6 g/l. During this stage of continuous/cell recycle mode of operation, a reactor productivity of 1.5 g muconic acid/liter/hour (0.1 hr$^{-1}$×15.6 g/l) is achieved. Muconic acid concentration in the cell-free fermentation broth is measured by High Performance Liquid Chromatograph (HPLC) with a C-18 column (silicone based reverse phase) 0.1 percent $H_3PO_4$/5.0 percent isopropyl alcohol mobile phase, and is detected by a UV detector at 254 nM.

The cell-free permeate rate from the ultrafilter to the first fermentation zone is then increased to 34–36 ml/min, and actively induced cells are introduced from a cell growth/enzyme induction second fermentation zone to the first fermentation zone at a flow rate of 12–15 ml/min. The operating conditions of the second fermentation zone are described in Section B.

The fermentor vapor phase (exit gas) toluene concentration control is increased to 0.75 mole percent or 0.8 mM dissolved toluene in the liquid phase. The toluene pump addition rate range is increased to 0.35–0.64 ml/min. Pure oxygen flow is increased to 250 cc/min and then to 500 cc/min to ensure sufficient oxygen mass transfer (supply) to the first fermentation zone broth and cells. During the transition stage (about 6–8 hours) from single-zone to two-zone continuous fermentation with cell recycle operation, the muconic acid concentration increases to 17.2 g/l and the cell concentration to 9.4 g/l. Both toluene and oxygen addition rates are further increased to 0.42–0.72 ml/min and 900 cc/min, respectively. A reactor purge of first fermentation zone broth (with cells) at a rate of 2–3 ml/min is initiated and maintained.

Twenty hours after starting the combined first fermentation zone and second fermentation zone mode of operation (66 hours after inoculation), the muconic acid concentration is 25–27 g/l and the cell concentration is 9.5–10 g/l. During this period of steady state continuous fermentation with second fermentation zone input and with cell recycle operation, a reactor productivity of 5.2 g muconic acid/l/hr (0.2 hr$^{-1}$×26 g/l) is achieved. The high reactor productivity is maintained for a period of 15 hours, and the combined fermentation operation is continued for a total of 60 hours.

B. Second Fermentation Zone

1. Inoculum Preparation

Inoculum preparation for the cell growth/enzyme induction fermentor is the same as described in Section A for the first fermentation zone.

2. Cell Growth/Enzyme Induction

After the inoculation, cells are allowed to grow for 8–10 hours to an optical density of 40–60 klett units. Toluene is then supplied to the fermentation medium in vapor phase via air stripping at an air-toluene vapor rate of 125 cc/min. The fermentation temperature is controlled at 30° C., the pH at 6.9 with 5 M ammonium hydroxide and 3 M sulfuric acid solutions, and the dissolved oxygen level at 30–90 percent saturation with 600 RPM agitation and 5 l/min aeration. Pluronic L61 polyol (BASF) is used as an antifoam agent.

As the optical density of the fermentation medium reaches 60–90 klett units (about 10–12 hours after inoculation), an aqueous solution of heat-sterilized Feed I is pumped into the second fermentation zone at a rate of 0.2 ml/min. The air-toluene vapor rate is increased to 250 cc/min and the Feed I rate to 0.4 ml/min as the optical density reaches 300 klett units. The air-toluene vapor rate is further increased to 500 cc/min and then to 750 cc/min as the optical density reaches 500–600 klett units. An aqueous solution of heat-sterilized Feed II is pumped into the fermentation medium at a rate of 0.4 ml/min.

3. Integrated Operation Of Fermentation Zones

Forty-eight hours after the inoculation, the muconic acid product concentration is 15 g/l and the cell concentration is 3.5 g/l in the second fermentation zone. The fed-batch mode of operation then is converted to a continuous operation and a stream of actively induced cells in the second fermentation zone is pumped into the first fermentation zone at a rate of 12–15 ml/min.

The air-toluene vapor rate to the second fermentation zone is increased to 1000 cc/min, and the Feed I and Feed II rates are increased to 0.6 ml/min during the transition from fed-batch to continuous operation.

Fresh, membrane-sterilized deionized water is pumped into the second fermentation zone at a rate of 12–15 ml/min. The level of the fermentation broth in the second fermentation zone is controlled at 11.5 liters with a New Brunswick Scientific level controller and a conductivity probe. Eight hours after the continuous operation, the Feed I and Feed II rates are increased to 0.9 ml/min to achieve a steady state cell concentration of 3.5 g/l and muconic acid concentration of 14 g/l.

The actively induced cells at a specific growth rate of 0.1 hr$^{-1}$ (equal to the dilution rate) in the second fermentation zone are fed continuously to the first fermentation throughout the combined operation of the two fermentation zones with cell recycle from the filtration zone.

EXAMPLE IV

This example illustrates an invention process embodiment with improved microbial stability of the recycled biocatalyst (cells) in both the first and second fermentation zones.

The inoculum preparations, cell growth/enzyme induction, continuous/cell recycle and combined fermentation zone operation procedures are the same as in Example III, with the following modifications:

(a) Sixteen hours after starting the continuous fermentation with cell recycle operation, the cell concentration in the first fermentation zone is 7–8 g/l, and the muconic acid product concentration is 14–16 g/l. The Feed I medium is replaced by a Feed III (Table 2) medium containing 200 g/l acetic acid, 31 g/l KOH and 22.2 g/l NaOH. The addition rates to the first fermentation zone are the same as those recited in Example III.

(b) Forty-eight hours after inoculation, the muconic acid product concentration reaches 12–15 g/l and cell concentration reaches 3.2–3.5 g/l in the second fermentation zone. The fed-batch mode of operation is converted to a continuous operation. The acetic acid concentration in the Feed I medium is increased from 200 g/l to 224 g/l. The addition rates to the second fermentation zone are the same as those recited in Example III.

The duration of high reactor productivity (4.8–5.2 g/l/hr) is maintained for a period of 48 hours, and the combined fermentation zone operation is continued for a total of 84 hours.

EXAMPLE V

This Example illustrates a continuous fermentation system with cell recycle and fermentation broth recycle for the production of muconic acid from toluene in accordance with, the process of copending patent application Serial Number 387,084 now U.S. Pat. No. 4,480,034.

A. Inoculum Preparation

A *Pseudomonas putida* Biotype A strain ATCC No. 31916 type of mutant strain culture (regular "NO" medium aqueous culture in polypropylene vial stored in liquid nitrogen) is thawed and transferred (1–1.5 ml) to a 250 ml shake flask containing 50 ml of regular "NO" medium with 5 mM sodium succinate as the growth carbon source, and is incubated at 30° C. (250 RPM) for nine hours to an optical density of 50–60 klett units.

The 50 ml culture is transferred to a 2.5 liter shake flask containing one liter of LP-1 medium (Table 1) with 20 mM sodium acetate as the carbon source and three polypropylene vials each with one ml toluene as the inducer, and is incubated at 30° C. (250 RPM) for 15 hours to an optical density of 60–90 klett units. The one liter culture is then inoculated into a 16 liter steam sterilizable fermentor (New Brunswick Scientific, Model SF 116) containing 11.5 liters of LP-1 medium with 20 mM of sodium acetate to start fermentation.

B. Enzyme Induction

After the inoculation toluene is supplied to the fermentor medium in vapor phase via air-stripping at an air-toluene vapor rate of 125 cc/min. The fermentation temperature is controlled at 30° C., the pH at 6.9 with 10N ammonium hydroxide and 6N sulfuric acid solution, and a dissolved oxygen level at 30–100% saturation with 500 to 600 RPM agitation and 5 l/min aeration (approximately 0.5 VVM). Pluronic L61 polyol (BASF) is used as an antifoam agent.

As the optical density of the fermentation medium reaches 60–90 klett units (about 6–9 hours after inoculation), an aqueous solution containing 10 weight percent acetic acid, 0.245 weight percent $KH_2PO_4$ and 0.128 weight percent $Na_2HPO_4$ is added to the fermentor medium at a rate of 0.4 ml/min. The air-toluene vapor rate is increased to 250 cc/min and then increased to 500 cc/min as the optical density reaches 250 klett units. The fed batch mode of fermentation is continued for 21 hours and the muconic acid product concentration reaches 12.6 g/l at a cell concentration of 2.1 g/l. The fermentation is then converted to a continuous operation with a cell recycle mode of operation.

C. Continuous/Cell Recycle

Starting the continuous/cell recycle operation, fresh membrane-sterilized LP-1 medium with 1.04 g/l acetic acid, 0.0256 g/l $KH_2PO_4$ and 0.0134 g/l $Na_2HPO_4$ concentration is pumped into the fermentor at a rate of 38.3 ml/min. The fermentation broth is pumped from the fermentor with an internal circulation pump to a Romicon hollow tube ultrafilter with a polysulfone type ultrafiltration membrane (PM-100; molecular weight cutoff of 100,000).

The fermentation broth with cells is "cross-flow" filtered by the ultrafilter controlled at a permeate (cell-free product stream) rate of 36–39 ml/min. The fermentation broth with cells is continuously circulated through the ultrafilter at an internal circulation rate of 4.5 l/min and a pressure drop of five to ten psig across the ultrafiltration membrane. Three hours after starting the continuous/cell recycle operation without purge, the cell concentration is 2.8 g/l. A purge stream at a rate of 2.7 ml/min is then maintained during the continuous/cell recycle run. After initial decrease, the product concentration in the cell-free permeate stream is maintained at 6.8–7.0 g/l at a permeate rate of 38 ml/min. The air-toluene vapor rate is increased to 1000 ml/min.

During this type of steady state continuous/cell recycle mode of operation, a reactor productivity of 1.4 g muconic acid/l/hr (0.20 $hr^{-1} \times 6.9$ g/l) is achieved and a specific productivity of 0.58 g muconic acid/g cells/hr (6.9 g/l$\times$0.2 $hr^{-1}$/2.4 g/l) is maintained.

D. Product Recovery And Fermentation Broth Recycle

The continuous operation is modified to include a product recovery procedure and a recycle of fermentation broth.

In the manner previously described, a solution of concentrated $H_2SO_4$ is added to the cell-free permeate to precipitate the muconic acid product. The precipitate is separated by filtration.

The acidic filtrate is neutralized with $CaCO_3$ which results in the formation and precipitation of $CaSO_4$ solids. The solids are separated by filtration.

The resultant fermentation broth filtrate, which contains $(NH_4)_2CO_3$ solute, is emulsified with toluene and air, sterilized, and then recycled to the fermentor. The quantity of $NH_4OH$ fed to the fermentor is reduced by an amount corresponding to the molar input of $(NH_4)_2CO_3$ contained in the recycled fermentation broth.

E. Adipic Acid Production

Muconic acid is dissolved in acetic acid to form a 40 percent muconic acid/acetic acid slurry solution.

The slurry solution is fed to a hydrogenation fixed-bed reactor (at 102° C. and 3 atm) with Pd/C as the catalyst.

The hydrogenation product solution is flashed and distilled to separate acetic acid. The heavy end slurry, which consists substantially of adipic acid, is washed to remove trace acetic acid, and dried.

TABLE 1

| | FERMENTATION MEDIA | | | |
|---|---|---|---|---|
| Chemicals (g/l) | Regular "NO" Medium | Modified "NO" Medium | LP-1 Medium | LP-2 Medium |
| $Na_2HPO_4$ | 7.1 | 7.1 | 1.42 | 0.0426 |
| $KH_2PO_4$ | 13.6 | 13.6 | 2.72 | 0.0817 |
| $(NH_4)_2SO_4$ | 2.25 | 0.281 | 0.749 | 2.24 |
| $MgSO_4.7H_2O$ | 0.246 | 0.738 | 0.738 | 0.738 |
| $CaCl_2.2H_2O$ | 0.0147 | 0.0294 | 0.0294 | 0.0294 |
| $FeSO_4.7H_2O$ | 0.00278 | 0.00834 | 0.00834 | 0.0167 |

All chemical concentrations are in g/l. Unless otherwise specified, the medium is prepared by adding appropriate growth carbon source in deionized water.

TABLE 2

| FEED MEDIA FOR CONTINUOUS OPERATION | | | |
|---|---|---|---|
| Chemicals (g/l) | Feed I | Feed II | Feed III |
| Acetic acid | 200 | — | 200 |
| $Na_2HPO_4$ | 2.27 | — | — |
| $KH_2PO_4$ | 4.36 | — | — |
| KOH | 31.0 | — | 31.0 |
| NaOH | 22.2 | — | 22.2 |
| $(NH_4)_2SO_4$ | — | 53.9 | — |
| $MgSO_4.7H_2O$ | — | 17.7 | — |
| $CaCl_2.2H_2O$ | — | 0.7 | — |
| $FeSO_4.7H_2O$ | — | 0.4 | — |

What is claimed is:

1. A continuous bioconversion process which comprises (1) continuously feeding toluene, an aqueous nutrient stream and molecular oxygen into a first fermentation zone containing a *Pseudomonas putida* Biotype A microorganism which bio-oxidizes the toluene to accumulated extracellular muconic acid product at a production rate of at least about 5 grams of muconic acid per liter of fermentation medium per hour; (2) continuously withdrawing whole cell-containing fermentation broth from the first fermentation zone and passing the withdrawn fermentation broth through a cross-flow membrane filtration zone to provide a whole cell-containing retentate stream and a cell-free muconic acid-containing permeate stream from the filtration zone; (3) recycling the retentate stream to the first fermentation zone, and recovering muconic acid product from the cell-free permeate stream; (4) continuously feeding toluene, an aqueous nutrient stream and molecular oxygen into a second fermentation zone containing the same microorganism as in the said first fermentation zone, under toluene-limited and growth carbon-limited conditions which favor cell growth and enzyme induction in the second fermentation zone, wherein the toluene in the second fermentation zone is limited to not more than about 0.1 millimole of toluene and the growth carbon is limited to not more than about 0.5 millimole of acetate or equivalent growth carbon source dissolved in the second fermentation zone medium; (5) continuously withdrawing a stream of whole cell-containing fermentation broth from the second fermentation zone and continuously passing the said stream into the first fermentation zone; and (6) withdrawing a purge stream of first fermentation zone whole cell-containing broth out of the fermentation system, at a monitored withdrawal rate for control of cell concentration at a level between about 6-12 grams dry weight per liter and a muconic acid productivity level of at least about 0.5 gram of muconic acid per dry weight gram of cells per hour in the said first fermentation zone.

2. A process in accordance with claim 1 wherein the microorganism exhibits enzymatic bio-oxidation activity characteristic of *Pseudomonas putida* Biotype A strain ATCC 31916 or a variant thereof for the bio-oxidation of toluene to accumulated extracellular muconic acid product.

3. A process in accordance with claim 1 wherein the microorganism is *Pseudomonas putida* Biotype A strain ATCC 31916.

4. A process in accordance with claim 1 wherein the concentration of muconic acid in the first fermentation zone is in the range between about 20-30 grams per liter of fermentation medium.

5. A process in accordance with claim 1 wherein the cell-containing purge stream is withdrawn from the first fermentation zone in a volume per hour which corresponds to about 1-10 percent of the volume of continuous feed stream into the first fermentation zone.

6. A process in accordance with claim 1 wherein the filtration zone comprises an ultrafiltration hollow fiber module.

7. A process in accordance with claim 1 wherein the filtration zone comprises an ultrafiltration plate and frame module.

8. A process in accordance with claim 1 wherein the toluene feed is partially or completely replaced with non-growth aromatic hydrocarbon selected from benzyl alcohol, benzaldehyde, benzoic acid and catechol.

* * * * *